US012781248B2

(12) United States Patent
Qi et al.

(10) Patent No.: US 12,781,248 B2
(45) Date of Patent: Nov. 3, 2026

(54) REDUCTION IN ACETATE PRODUCTION BY YEAST OVER-EXPRESSING MIG3

(71) Applicant: DANISCO US INC, Palo Alto, CA (US)

(72) Inventors: Min Qi, Hockessin, DE (US); Quinn Qun Zhu, West Chester, PA (US); Jamie Yehong Wang, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 1061 days.

(21) Appl. No.: 17/779,753

(22) PCT Filed: Nov. 24, 2020

(86) PCT No.: PCT/US2020/062109

§ 371 (c)(1),
(2) Date: May 25, 2022

(87) PCT Pub. No.: WO2021/108464

PCT Pub. Date: Jun. 3, 2021

(65) Prior Publication Data

US 2023/0002793 A1 Jan. 5, 2023

Related U.S. Application Data

(60) Provisional application No. 62/940,510, filed on Nov. 26, 2019.

(51) Int. Cl.

| | |
|---|---|
| ***C12P 7/06*** | (2006.01) |
| ***C12N 1/185*** | (2026.01) |
| ***C12N 15/52*** | (2006.01) |
| ***C12R 1/865*** | (2006.01) |

(52) U.S. Cl.

CPC ................ *C12P 7/06* (2013.01); *C12N 1/185* (2021.05); *C12N 15/52* (2013.01); *C12Y 102/04001* (2013.01); *C12Y 203/01008* (2013.01); *C12Y 401/02009* (2013.01); *C12R 2001/865* (2021.05)

(58) Field of Classification Search

None

See application file for complete search history.

(56) References Cited

U.S. PATENT DOCUMENTS

| | | | | |
|---|---|---|---|---|
| 8,795,998 | B2 | 8/2014 | Pronk et al. | |
| 8,956,851 | B2 | 2/2015 | Argyros et al. | |
| 9,175,270 | B2 | 11/2015 | Nevoigt et al. | |
| 2012/0064591 | A1 | 3/2012 | Gasch et al. | |
| 2019/0338256 | A1* | 11/2019 | Miasnikov | C12Y 203/01008 |

FOREIGN PATENT DOCUMENTS

| | | | |
|---|---|---|---|
| CN | 104974945 | A | 10/2015 |
| CN | 105602862 | A | 5/2016 |
| WO | 2013081700 | A1 | 6/2013 |
| WO | 2015023989 | A1 | 2/2015 |
| WO | 2015148272 | A1 | 10/2015 |
| WO | 2018176021 | A1 | 9/2018 |
| WO | 2019173204 | A1 | 9/2019 |

OTHER PUBLICATIONS

Chica et al. Curr Opin Biotechnol. Aug. 2005;16(4):378-84. (Year: 2005).*

Singh et al. Curr Protein Pept Sci. 2017, 18, 1-11 (Year: 2017).*

Kizer et al. Appl Environ Microbiol. May 2008;74(10):3229-41. (Year: 2008).*

Prather et al. Curr Opin Biotechnol. Oct. 2008;19(5):468-74. (Year: 2008).*

Altschul et al., "Basic Local Alignment Search Tool", J. Mol. Biol., vol. 215, 1990, pp. 403-410.

Altschul et al., "Local Alignment Statistics", Meth. Enzymol., vol. 266, 1996, pp. 460-480.

Devereux et al., "A comprehensive set of sequence analysis programs for the VAX", Nucleic Acids Res., vol. 12, 1984, pp. 387-395.

Duskova et al., "Two glycerol uptake systems contribute to the high osmotolerance of Zygosaccharomyces rouxii", Mol. Microbiol., vol. 97, 2015, pp. 541-559.

Feng et al., "Progressive Sequence Alignment as a Prerequisite to Correct Phylogenetic Trees", J. Mol. Evol., vol. 35, 1987, pp. 351-360.

Ferreira et al., "A Member of the Sugar Transporter Family, Stl1p Is the Glycerol/H Symporter in *Saccharomyces cerevisiae*" Mol. Biol. Cell, vol. 16, 2005, pp. 2068-2076.

Gombert et al., "Improving conversion yield of fermentable sugars into fuel ethanol in 1st generation yeast-based production processes", Curr. Opin. Biotechnol., vol. 33, 2015, pp. 81-86.

Henikoff et al., "Amino acid substitution matrices from protein blocks", Proc. Natl. Acad. Sci. USA, vol. 89, 1989, pp. 10915-10919.

Higgins et al., "Fast and sensitive multiple sequence alignments on a microcomputer", CABIOS, vol. 5, 1989, pp. 151-153.

Karlin et al., "Applications and statistics for multiple high-scoring segments in molecular sequences", Proc. Natl. Acad. Sci. USA, vol. 90, 1993, pp. 5873-5887.

Karunanithi et al., "The Filamentous Growth MAPK Pathway Responds to Glucose Starvation Through the Mig1/2 Transcriptional Repressors in *Saccharomyces cerevisiae*", Genetics, vol. 192, No. 3, Nov. 2012, pp. 869-887.

Lewis et al., "Natural Variation in the Yeast Glucose-Signaling Network Reveals a New Role for the Mig3p Transcription Factor" G3, vol. 2, 2012, pp. 1607-1612.

(Continued)

*Primary Examiner* — Christian L Fronda

(57) ABSTRACT

Described are compositions and methods relating to modified yeast that over-express MIG transcriptional regulator polypeptides. The yeast produces a deceased amount of acetate compared to parental cells. Such yeast is particularly useful for large-scale ethanol production from starch substrates where acetate in an undesirable end product.

12 Claims, No Drawings

Specification includes a Sequence Listing.

(56) References Cited

OTHER PUBLICATIONS

Needleman et al., "A General Method Applicable to the Search for Similarities in the Amino Acid Sequence of Two Proteins", J. Mol. Biol. vol. 48, 1970, pp. 443-453.
Pearson et al., "Improved tools for biological sequence comparison", Proc. Natl Acad. Sci. USA, vol. 85, 1988, pp. 2444-2448.
Shankar et al., "MIG1 overexpression causes flocculation in *Saccharomyces cerevisiae*", Microbiology, vol. 142, part 9, Sep. 1996, pp. 2663-2667.
Smith et al., Adv. Appl. Math., "Comparison of Biosequences", vol. 2, 1981, pp. 482-489.
Takahashi et al., "Overexpression of FAP7, MIG3, TMA19, or YLR392c confers resistance to arsenite on *Saccharomyces cerevisiae*", Journal of Toxicological Sciences, vol. 35, No. 6, Jan. 2010, pp. 945-946.
Thompson et al., "CLUSTAL W: improving the sensitivity of progressive multiple sequence alignment through sequence weighting, position-specific gap penalties and weight matrix choice", Nucleic Acids Res., vol. 22, 1994, pp. 4673-4680.
Zhang et al., "Engineering of the glycerol decomposition pathway and cofactor regulation in an industrial yeast improves ethanol production", J. Ind. Microbiol. Biotechnol., vol. 40, 2013, pp. 1153-1160.
International Search Report and Written Opinion from PCT Application No. PCT/US2020/062109 dated Mar. 1, 2021, 13 pages.

* cited by examiner

REDUCTION IN ACETATE PRODUCTION BY YEAST OVER-EXPRESSING MIG3

TECHNICAL FIELD

The present compositions and methods relate to modified yeast that over-expresses MIG transcription regulator polypeptides. The yeast produces a deceased amount of acetate compared to parental cells. Such yeast is particularly useful for large-scale ethanol production from starch substrates, where acetate in an undesirable by-product.

BACKGROUND

First-generation yeast-based ethanol production converts sugars into fuel ethanol. The annual fuel ethanol production by yeast is about 90 billion liters worldwide (Gombert, A. K. and van Maris. A. J. (2015) *Curr. Opin. Biotechnol.* 33:81-86). It is estimated that about 70%/6 of the cost of ethanol production is the feedstock. Since the production volume is so large, even small yield improvements have massive economic impact across the industry.

Ethanol production in engineered yeast cells with a heterologous phosphoketolase (PKL) pathway is higher than in a parental strain without a PKL pathway (see, e.g., Miasnikov et al. WO2015148272). The PKL pathway consists of phosphoketolase (PKL) and phosphotransacetylase (PTA) to channel carbon flux away from the glycerol pathway and toward the synthesis of acetyl-coA. Two supporting enzymes, acetaldehyde dehydrogenase (AADH) and acetyl-coA synthase (ACS), can help the PKL pathway be more effective.

Unfortunately, the engineered strains also produce more acetate than the parental yeast. Acetate is not a desirable by-product as it has negative effects on yeast growth and fermentation. In addition, acetate reduces the pH of left-over water from fermentation and distillation, referred to as backset, which is typically reused for liquefaction of a subsequent batch of substrate. As a result, ethanol producers must adjust the pH of the backset (or liquefact) or increase the amount of fresh water used for liquefaction.

The need exists to control the amount of acetate produced by yeast, particularly engineered yeast that tend to produce an increased amount of acetate.

SUMMARY

The present compositions and methods relate to modified yeast that over-express the MIG transcription regulator polypeptides. Aspects and embodiments of the compositions and methods are described in the following, independently-numbered, paragraphs.

1. In one aspect, modified yeast cells derived from parental yeast cells are provided, the modified cells comprising a genetic alteration that causes the modified cells to produce during fermentation an increased amount of MIG transcription regulator polypeptides compared to otherwise identical parental cells, wherein the modified cells produce during fermentation a decreased amount of acetate compared to the amount of acetate produced by the otherwise identical parental cells under identical fermentation conditions.
2. In some embodiments of the modified cells of paragraph 1, the genetic alteration comprises the introduction into the parental cells of a nucleic acid capable of directing the expression of a MIG transcription regulator polypeptide to a level above that of the parental cell grown under equivalent conditions.
3. In some embodiments of the modified cells of paragraph 1, the genetic alteration comprises the introduction of new promoter for expressing a MIG transcription regulator polypeptide.
4. In some embodiments of the modified cells of any of paragraphs 1-3, the cells further comprise one or more genes of the phosphoketolase pathway.
5. In some embodiments of the modified cells of paragraph 4, the genes of the phosphoketolase pathway are selected from the group consisting of phosphoketolase, phosphotransacetylase and acetylating acetyl dehydrogenase.
6. In some embodiments of the modified cells of any of paragraphs 1-5, the amount of increase in the expression of the MIG transcription regulator polypeptide is at least 20%, at least 30%, at least 40%, at least 50%, at least 70%, at least 100%, at least 150%, at least 2000%, at least 500%, at least 1,000%, at least 2,000%, or more, compared to the amount of MIG transcription regulator polypeptides produced by parental cells grown under the same conditions.
7. In some embodiments of the modified cells of any of paragraphs 1-5, the amount of increase in the production of mRNA encoding the MIG transcription regulator polypeptide is at least 2-fold, at least 5-fold, at least 10-fold, at least 20-fold, at least 50-fold, at least 100-fold or more, compared to the level in the parental cells grown under equivalent conditions.
8. In some embodiments of the modified cells of any of paragraphs 1-7, the cells further comprise an exogenous gene encoding a carbohydrate processing enzyme.
9. In some embodiments, the modified cells of any of paragraphs 1-8 further comprises an alteration in the glycerol pathway and/or the acetyl-CoA pathway.
10. In some embodiments, the modified cells of any of paragraphs 1-9 further comprise an alternative pathway for making ethanol.
11. In some embodiments of the modified cells of any of paragraphs 1-10, the cells are of a *Saccharomyces* spp.
12. In some embodiments of the modified cells of any of paragraphs 1-11, the MIG transcription regulator polypeptide is MIG1, MIG2, MIG3 or a combination, thereof.
13. In another aspect, a method for decreasing the production of acetate from yeast cells grown on a carbohydrate substrate is provided, comprising: introducing into parental yeast cells a genetic alteration that increases the production of MIG transcription regulator polypeptides compared to the amount produced by the parental cells.
14. In some embodiments of the method of paragraph 13, the cells having the introduced genetic alteration are the modified cells are the cells of any of paragraphs 1-12.
15. In some embodiments of the method of paragraph 13 or 14, the decrease in acetate production is at least 5%, at least 10%, at least 15%, at least 20%, at least 25%, at least 30%, at least 35%, at least 40%, at least 50%1%, at least 60%, or more.
16. In some embodiments of the method of any of paragraphs 13-15, MIG transcription regulator polypeptides are over-expressed by is at least 20%, at least 30%, at least 40%, at least 50%, at least 70%, at least 100%, at least 150%, at least 200%, at least 5000%, at least 1,000%, at least 2,000%, or more, compared to the amount of MIG transcription regulator polypeptides produced by otherwise identical parental cells grown under the same conditions.

17. In some embodiments of the method of any of paragraphs 13-16, MIG transcription regulator mRNA is over-expressed by at least 2-fold, at least 5-fold, at least 10-fold, at least 20-fold, at least 50-fold, at least 100-fold or more, compared to the amount produced in the parental cells grown under equivalent conditions.

These and other aspects and embodiments of present modified cells and methods will be apparent from the description, including any accompanying Drawings/FIGURES.

DETAILED DESCRIPTION

I. Definitions

Prior to describing the present yeast and methods in detail, the following terms are defined for clarity. Terms not defined should be accorded their ordinary meanings as used in the relevant art.

As used herein, the term "alcohol" refers to an organic compound in which a hydroxyl functional group (—OH) is bound to a saturated carbon atom.

As used herein, the terms "yeast cells," "yeast strains," or simply "yeast" refer to organisms from the phyla Ascomycota and Basidiomycota. Exemplary yeast is budding yeast from the order Saccharomycetales. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "engineered yeast cells," "variant yeast cells," "modified yeast cells," or similar phrases, refer to yeast that include genetic modifications and characteristics described herein. Variant/modified yeast do not include naturally occurring yeast.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins," or "homologs." Such proteins can be derived from organisms of different genera and/or species, or different classes of organisms (e.g., bacteria and fungi), or artificially designed. Related proteins also encompass homologs determined by primary sequence analysis, determined by secondary or tertiary structure analysis, or determined by immunological cross-reactivity, or determined by their functions.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.,* 48:443; Pearson and Lipman (1988)*Proc. Natl. Acad Sci*. USA 85:2444; programs such as GAP, BESTFIT, FASTA, and TFASTA in the Wisconsin Genetics Software Package (Genetics Computer Group, Madison, WI); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sd. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: HUB
Delay divergent sequences %: 40

Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype. The term "allele" is generally preferred when an organism contains more than one similar genes, in which case each different similar gene is referred to as a distinct "allele."

As used herein, "constitutive" expression refers to the production of a polypeptide encoded by a particular gene under essentially all typical growth conditions, as opposed to "conditional" expression, which requires the presence of a particular substrate, temperature, or the like to induce or activate expression.

As used herein, the term "expressing a polypeptide" and similar terms refers to the cellular process of producing a polypeptide using the translation machinery (e.g., ribosomes) of the cell.

As used herein, "over-expressing a polypeptide," "increasing the expression of a polypeptide," and similar terms, refer to expressing a polypeptide at higher-than-normal levels compared to those observed with parental or "wild-type cells that do not include a specified genetic modification.

As used herein, an "expression cassette" refers to a DNA fragment that includes a promoter, and amino acid coding region and a terminator (i.e., promoter::amino acid coding region::terminator) and other nucleic acid sequence needed to allow the encoded polypeptide to be produced in a cell. Expression cassettes can be exogenous (i.e., introduced into a cell) or endogenous (i.e., extant in a cell).

As used herein, the terms "fused" and "fusion" with respect to two DNA fragments, such as a promoter and the coding region of a polypeptide refer to a physical linkage causing the two DNA fragments to become a single molecule.

As used herein, the terms "wild-type" and "native" are used interchangeably and refer to genes, proteins or strains found in nature, or that are not intentionally modified for the advantage of the presently described yeast.

As used herein, the term "protein of interest" refers to a polypeptide that is desired to be expressed in modified yeast. Such a protein can be an enzyme, a substrate-binding protein, a surface-active protein, a structural protein, a selectable marker, or the like, and can be expressed. The protein of interest is encoded by an endogenous gene or a heterologous gene (i.e., gene of interest") relative to the parental strain. The protein of interest can be expressed intracellularly or as a secreted protein.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using CRISPR, RNAi, antisense, or any other method that abolishes gene expression. A gene can be disrupted by deletion or genetic manipulation of non-adjacent control elements. As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences, but does not require the deletion of non-adjacent control elements. Deletion of a gene also refers to the deletion a part of the coding sequence, or a part of promoter immediately or not immediately adjacent to the coding sequence, where there is no functional activity of the interested gene existed in the engineered cell.

As used herein, the terms "genetic manipulation," "genetic alteration", "genetic engineering", and similar terms are used interchangeably and refer to the alteration/change of a nucleic acid sequence. The alteration can include but is not limited to a substitution, deletion, insertion or chemical modification of at least one nucleic acid in the nucleic acid sequence.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein, "attenuation of a pathway" or "attenuation of the flux through a pathway," i.e., a biochemical pathway, refers broadly to any genetic or chemical manipulation that reduces or completely stops the flux of biochemical substrates or intermediates through a metabolic pathway.

Attenuation of a pathway may be achieved by a variety of well-known methods. Such methods include but are not limited to: complete or partial deletion of one or more genes, replacing wild-type alleles of these genes with mutant forms encoding enzymes with reduced catalytic activity or increased Km values, modifying the promoters or other regulatory elements that control the expression of one or more genes, engineering the enzymes or the mRNA encoding these enzymes for a decreased stability, misdirecting enzymes to cellular compartments where they are less likely to interact with substrate and intermediates, the use of interfering RNA, and the like.

As used herein, "aerobic fermentation" refers to growth and production process in the presence of oxygen.

As used herein, "anaerobic fermentation" refers to growth and production in the absence of oxygen.

As used herein, the expression "end of fermentation" refers to the stage of fermentation when the economic advantage of continuing fermentation to produce a small amount of additional alcohol is exceeded by the cost of continuing fermentation in terms of fixed and variable costs. In a more general sense, "end of fermentation" refers to the point where a fermentation will no longer produce a significant amount of additional alcohol, i.e., no more than about 1% additional alcohol.

As used herein, the expression "carbon flux" refers to the rate of turnover of carbon molecules through a metabolic pathway. Carbon flux is regulated by enzymes involved in metabolic pathways, such as the pathway for glucose metabolism and the pathway for maltose metabolism.

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

following meanings unless otherwise specified:

° C. degrees Centigrade
AA α-amylase
AADH acetaldehyde dehydrogenases
bp base pairs
DNA deoxyribonucleic acid
ds or DS dry solids
EC enzyme commission
EtOH ethanol
g or gm gram
g/L grams per liter
GA glucowmylase
$H_2O$ water
HPLC high performance liquid chromatography
hr or h hour
kg kilogram
M molar
mg milligram
min minute
mL or ml milliliter
mM millimolar
N normal
nm nanometer
PCR polymerase chain reaction
PKL phosphoketolase
ppm parts per million
PTA phosphotransacetylase
Δ relating to a deletion
βg microgram
µL and µl microliter
µM micromolar

II. Modified Yeast Cells Having Increased MIG Expression

Described are modified yeast and methods involving a genetic alteration that results in the production of increased amounts of MIG transcription regulator polypeptides compared to corresponding (i.e., otherwise-identical) parental cells. MIG transcription regulator polypeptides (or simply MIG transcription regulators) are a family of $Cys_2His_2$ zinc finger proteins. MIG1 is 504 amino acid in length. MIG2 is 383 amino acid in length and MIG3 is 395 amino acid in length. Overall amino acid sequence identity is less than 30% among these transcription factors, but they share>70% sequence identity in their DNA binding domains.

MIG1 and MIG2 play well-defined roles in glucose-responsive repression of genes involved in gluconeogenesis, aerobic respiration, and alternative carbon-source utilization. Much less is known for the function of MIG3. A recent study showed that MIG3 has a role in catabolite repression and an additional regulatory role upon ethanol exposure in some strains (Lewis, J. A. and Gasch, A. P. (2012) G3 2:1607-12). However, no association has heretofore been made between MIG over-expression and reduced acetate production in yeast fermentation for ethanol production.

Applicants have discovered that yeast cells over-expressing MIG1, MIG2 and MIG3 transcription regulator polypeptides produce during fermentation decreased amounts of acetate compared to otherwise-identical parental cells. Decreased acetate is desirable as acetate adversely affects yeast growth and fermentation and additionally results in backset that has a lower than desirable pH, requiring pH adjustment or the use of more fresh water to dilute the backset.

In some embodiments, the increase in the amount of MIG polypeptides produced by the modified cells is an increase of at least 20%, at least 30%, at least 40%, at least 50%, at least 70%, at least 100%, at least 150%, at least 200%, at least 500%, at least 1,000%, at least 2,000%, or more, compared to the amount of MIG polypeptides produced by parental cells grown under the same conditions.

In some embodiments, the increase in the amount of MIG mRNA produced by the modified cells is at least 2-fold, at least 5-fold, at least 10-fold, at least 20-fold, at least 50-fold, at least 100-fold or more, compared to the amount of MIG mRNA produced by parental cells grown under the same conditions.

In some embodiments, the increase in the strength of the promoter used to control expression of the MIG polypeptides produced by the modified cells is at least 2-fold, at least 5-fold, at least 10-fold, at least 20-fold, at least 50-fold, at least 100-fold or more, compared to strength of the native promoter controlling MIG expression, based on the amount of mRNA produced.

In some embodiments, the decrease in acetate production by the modified cells is a decrease of at least 5%, at least 10/a, at least 15%, at least 20%, at least 25%, at least 30%, at least 35/a, at least 40%, at least 50/o, at least 60% or more, compared to the amount of acetate produced by parental cells grown under the same conditions.

Preferably, increased MIG expression is achieved by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

In some embodiments, the present compositions and methods involve introducing into yeast cells a nucleic acid capable of directing the over-expression, or increased expression, of a MIG polypeptide. Particular methods include but are not limited to (i) introducing an exogenous expression cassette for producing the polypeptide into a host cell, optionally in addition to an endogenous expression cassette, (ii) substituting an exogenous expression cassette with an endogenous cassette that allows the production of an increased amount of the polypeptide, (iii) modifying the promoter of an endogenous expression cassette to increase expression, and/or (iv) modifying any aspect of the host cell to increase the half-life of the polypeptide in the host cell.

In some embodiments, the parental cell that is modified already includes a gene of interest, such as a gene encoding a selectable marker, carbohydrate-processing enzyme, or other polypeptide. In some embodiments, a gene of introduced is subsequently introduced into the modified cells.

The amino acid sequence of the exemplified *S. cerevisiae* MIG1 polypeptide is shown, below, as SEQ ID NO: 5:

```
MQSPYPMTQVSNVDDGSLLKESKSKSKVAAKSEAPRPHACPICHRAFHRL

EHQTRHMRIHTGEKPHACDFPGCVKRFSRSDELTRHRRIHTNSHPRGKRG

RKKKVVGSPINSASSSATSIPDLNTANFSPPLPQQHLSPLIPIAIAPKEN

SSRSSTRKGRKTKFEIGESGGNDPYMVSSPKTMAKIPVSVKPPPSLALNN

MNYQTSSASTALSSLSNSHSGSRLKLNALSSLQMMTPIASSAPRTVFIDG

PEQKQLQQQQNSLSPRYSNTVILPRPRSLTDFQGLNNANPNNNGSLRAQT

QSSVQLKRPSSVLSLNDLLVGQRNTNESDSDFTTGGEDEEDGLKDPSNSS

IDNLEQDYLQEQSRKKSKTSTPTTMLSRSTSGTNLHTLGYVMNQNHLHFS

SSSPDFQKELNNRLLNVQQQQQEQHTLLQSQNTSNQSQNQNQNQMMASSS

SLSTTPLLLSPRVNMINTAISTQQTPISQSDSQVQELETLPPIRSLPLPP

PHMD
```

The amino acid sequence of the exemplified *S. cerevisiae* MIG2 polypeptide is shown, below, as SEQ ID NO: 7:

```
MPKKQTNFPVDNENRPFRCDTCHRGFHRLEHKKRHLRTHTGEKPHHCAFP

GCGKSFSRSDELKRHMRTHTGQSQRRLKKASVQKQEFLTVSGIPTIASGV

MIHQPIPQVLPANMAINVQAVNGGNIIHAPNAVHPMVIPIMAQPAPIHAS

AASFQPATSPMPISTYTPVPSQSFTSFQSSIGSIOSNSDVSSIFSNMNVR

VNTPRSVPNSPNDGYLHQQHIPQQYQHQTASPSVAKQQKTFAHSLASALS

TLQKRTPVSAPSTTIESPSSPSDSSHTSASSSAISLPFSNAPSQLAVAKE

LESVYLDSNRYTTKTRRERAKFEIPEEQEEDTNNSSSGSNEEEHESLDHE

SSKSRKKLSGVKLPPVRNLLKQIDVFNGPKRV
```

The amino acid sequence of the exemplified *S. cerevisiae* MIG3 polypeptide is shown, below, as SEQ ID NO: 1:

```
MNYLRDRFPPDNDQRPFRCEICSRGFHRLEHKKRHVRTHTGEKPHKCTVQ

GCPKSFSRSDELKRHLRTHTKGVQRRRIKSKGSRKTVVNTATAAPTTFNE

NTGVSLTGIGQSKVPPILISVAQNCDDVNIRNTGNNNGIVETQAPAILVP

VINIPNDPHPIPSSLSTTSITSIASVYPSTSPFQYLKSGFPEDPASTPYV

HSSGSSLALGELSSNSSIFSKSRRNLAAMSGPDSLSSSKNQSSASLLSQT
```

-continued

```
SHPSKSFSRPPTDLSPLRRIMPSVNTGDMEISRTVSVSSSSSSLTSVTYD

DTAAKDMGMGIFFDRPPVTQKACRSNHKYKVNAVSRGRQHERAQFHISGD

DEDSNVHRQESRASNTSPNVSLPPIKSILRQIDNFNSAPSYFSK
```

The NCBI database includes numerous *S. cerevisiae* MIG polypeptides. While amino acid sequence identity among MIG1, MIG2 and MIG3 is highest in the DNA-binding domains, natural variations throughout the amino acid sequences MIG1, MIG2 and MIG3 are not expected to affect their function. In addition, it is apparent that the exemplified *S. cerevisiae* MIG1, MIG2 and MIG3 polypeptide shares sequence identity to polypeptides from other organisms, and over-expression of functionally and/or structurally similar proteins, homologous proteins and/or substantially similar or identical proteins, is expected to produce similar beneficial results.

In particular embodiments of the present compositions and methods, the amino acid sequence of the MIG1, MIG2 and/or MIG3 polypeptide that is over-expressed in modified yeast cells has at least about 50%, at least about 60%, at least about 70%, at least about 80%, at least about 90%, at least about 91%, at least about 92%, at least about 93%, at least about 94%, at least about 95%, at least about 96%, at least about 97%, at least about 98%, or even at least about 99% identity, to SEQ ID NO: 5, SEQ ID NO: 7 and/or SEQ ID NO: 1, respectively.

III. Modified Yeast Cells Having Increased MIG Transcription Regulator Expression in Combination with Genes of an Exogenous PKL Pathway Increased expression of MIG transcription regulators can be combined with expression of genes in the PKL pathway to reduce the production of elevated amounts of acetate that is associated with introducing an exogenous PKL pathway into yeast.

Engineered yeast cells having a heterologous PKL pathway have been previously described in WO2015148272 (Miasnikov et al.). These cells express heterologous phosphoketolase (PKL), phosphotransacetylase (PTA) and acetylating acetyl dehydrogenase (AADH), optionally with other enzymes, to channel carbon flux away from the glycerol pathway and toward the synthesis of acetyl-CoA, which is then converted to ethanol. Such modified cells are capable of increased ethanol production in a fermentation process when compared to otherwise-identical parent yeast cells.

IV. Combination of Increased MIG Transcription Regulator Production with Other Mutations that Affect Alcohol Production In some embodiments, in addition to expressing increased amounts of MIG polypeptides, optionally in combination with a heterologous PKL pathway, the present modified yeast cells include additional beneficial modifications.

The modified cells may further include mutations that result in attenuation of the native glycerol biosynthesis pathway and/or reuse glycerol pathway, which are known to increase alcohol production. Methods for attenuation of the glycerol biosynthesis pathway in yeast are known and include reduction or elimination of endogenous NAD-dependent glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat. No. 9,175,270 (Elke et al.), 8,795,998 (Pronk et al.) and 8,956,851 (Argyros et al.). Methods to enhance the reuse glycerol pathway by over expression of glycerol dehydrogenase (GCYI) and dihydroxyacetone kinase (DAKI) to convert glycerol to dihydroxyacetone phosphate (Zhang et al. (2013) *J. Ind Microbiol. Biotechnol.* 40:1153-60).

The modified yeast may further feature increased acetyl-CoA synthase (also referred to acetyl-CoA ligase) activity (EC 6.2.1.1) to scavenge (i.e., capture) acetate produced by chemical or enzymatic hydrolysis of acetyl-phosphate (or present in the culture medium of the yeast for any other reason) and converts it to Ac-CoA. This partially reduces the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like.

In some embodiments the modified cells may further include a heterologous gene encoding a protein with $NAD^+$-dependent acetylating acetaldehyde dehydrogenase activity and/or a heterologous gene encoding a pyruvate-formate lyase. The introduction of such genes in combination with attenuation of the glycerol pathway is described, e.g., in U.S. Pat. No. 8,795,998 (Pronk et al.). In some embodiments of the present compositions and methods the yeast expressly lacks a heterologous gene(s) encoding an acetylating acetaldehyde dehydrogenase, a pyruvate-formate lyase or both.

In some embodiments, the present modified yeast cells may further over-express a sugar transporter-like (STL1) polypeptide to increase the uptake of glycerol (see, e.g., Ferreira et al. (2005) *Mol. Biol Cell.* 16:2068-76; Dušková et al. (2015) *Mol. Microbiol.* 97:541-59 and WO2015023989 A1) to increase ethanol production and reduce acetate.

In some embodiments, the present modified yeast cells further include a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, over-expression, and/or substitution in one or more endogenous polynucleotides encoding FRA2, ALD6, ADH1, GPD2, BDH1, DLS1, DPB3, CPR1, MAL23C, MNN4, PAB1, TMN2, HAC1, PTC1, PTC2, OSM1, GIS1, CRZ1, HUG1, GDS1, CYB2P, SFC1, MVB12, LDB10, CSSD, GIC1, GIC2 and/or YMR226C.

V. Combination of Increased MIG Transcription Regulator Expression with Other Beneficial Mutations In some embodiments, in addition to increased expression of MIG polypeptides, optionally in combination with other genetic modifications that benefit alcohol production, the present modified yeast cells further include any number of additional genes of interest encoding proteins of interest. Additional genes of interest may be introduced before, during, or after genetic manipulations that result in the increased production of active MIG polypeptides. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transladolase, an epimerase, a phytase, a xylanase, a β-glucanase, a phosphatase, a protease, an α-amylase, a β-arnylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VI. Use of the Modified Yeast for Increased Alcohol Production

The present compositions and methods include methods for increasing alcohol production and/or reducing glycerol production, in fermentation reactions. Such methods are not limited to a particular fermentation process. The present engineered yeast is expected to be a "drop-in" replacement for convention yeast in any alcohol fermentation facility. While primarily intended for fuel alcohol production, the present yeast can also be used for the production of potable alcohol, including wine and beer.

VII. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces*, Lachancea and *Schizosaccharomyces* spp. Numerous yeast strains are commercially available, many of which have been selected or genetically engineered for desired characteristics, such as high alcohol production, rapid growth rate, and the like. Some yeasts have been genetically engineered to produce heterologous enzymes, such as glucoamylase or α-amylase.

VI. Substrates and Products

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

These and other aspects and embodiments of the present yeast strains and methods will be apparent to the skilled person in view of the present description. The following examples are intended to further illustrate, but not limit, the compositions and methods.

EXAMPLES

Example 1

Materials and Methods

Liquefact Preparation:

Liquefact (corn mash slurry) was prepared by adding 600 ppm of urea, 0.124 SAPU/g ds acid fungal protease, 0.33 GAU/g ds variant *Trichoderma reesei* glucoamylase and 1.46 SSCU/g ds *Aspergillus kawachii* α-amylase, adjusted to a pH of 4.8 with sulfuric acid.

Serum Vial Assays:

2 mL of YPD in 24-well plates were inoculated with yeast cells and the cultures allowed to grow overnight to an OD between 25-30. 2.5 mL liquefact was transferred to serum vials (Chemglass, Catalog No. CG-4904-01) and yeast was added to each vial to a final OD of about 0.4-0.6. The lids of the vials were installed and punctured with needle (BD, Catalog No. 305111) for ventilation (to release $CO_2$), then incubated at 32° C. with shaking at 200 RPM for 65 hours.

AnKom Assays:

300 μL of concentrated yeast overnight culture was added to each of a number ANKOM bottles filled with 50 g prepared liquefact (see above) to a final OD of 0.3. The bottles were then incubated at 32° C. with shaking at 150 RPM for 65 hours.

HPLC Analysis:

Samples of the cultures from serum vials and AnKom assays were collected in Eppendorf tubes by centrifugation for 12 minutes at 14,000 RPM. The supernatants were filtered using 0.2 μM PTFE filters and then used for HPLC (Agilent Technologies 1200 series) analysis with the following conditions: Bio-Rad Aminex HPX-87H columns, running temperature of 55 C. 0.6 ml/min isocratic flow 0.01 N $H_2SO_4$, 2.5 μl injection volume. Calibration standards were used for quantification of the of acetate, ethanol, glycerol, glucose and other molecules. All values are reported in g/L.

RNA-Seq Analysis:

RNA was prepared from individual samples according to the TRIzol method (Life-Tech, Rockville, MD). The RNA was then cleaned up with Qiagen RNeasy Mini Kit (Qiagen, Germantown, MD). The cDNA from total mRNA in individual samples was generated using Applied Biosystems High Capacity cDNA Reverse Transcription kit (Thermo Fisher Scientific, Wilmington, Delaware). The prepared cDNA of each sample was sequenced using the shotgun method, and then quantified with respect to individual genes. The results are reported as reads per kilobase ten million transcripts (RPK10M), and used to quantify the amount of each transcript in a sample.

Example 2

Expression of MIG in Yeast

To understand the regulation of MIG in yeast, RNA-Seq analysis was performed on *Saccharomyces cerevisiae* strain FERMAX™ Gold (Martrex Inc., Minnesota, USA; herein abbreviated "FG"), a standard strain used for ethanol production. RNA-Seq was performed as described in Example 1 and the results are summarized in Table 1. Expression levels are expressed as reads per kilobase ten million transcripts (RPK10M).

TABLE 1

RNA-Seq analysis of MIG expression in FG during fermentation

| | Time | | | | |
|---|---|---|---|---|---|
| Gene | 6 hr | 12 hr | 24 hr | 36 hr | 48 hr |
| MIG1 | 353 | 472 | 468 | 241 | 293 |
| MIG2 | 214 | 359 | 618 | 238 | 282 |
| MIG3 | 375 | 450 | 561 | 309 | 305 |

The results indicate that MIG1, MIG2 and MIG3 are expressed at low levels during fermentation in the FG strain. Relatively, MIG3 is expressed at the highest level at approximately 24 hr during fermentation.

Example 3

Promoter Selection for Increased Expression of MIG3

As shown in Table 2, translation elongation factor 1 β (EFB1) was expressed at the highest level at approximately 6 hr during fermentation, then maintained high level expression during the remainder fermentation in the FG strain. Consequently, the EFB1 promoter was selected to drive over-expression of MIG3.

TABLE 2

Transcription profiles of MIG3 and EFB1 during fermentation

| | Time | | | | |
|---|---|---|---|---|---|
| Gene | 6 hr | 12 hr | 24 hr | 36 hr | 48 hr |
| MIG3 | 375 | 450 | 561 | 309 | 305 |
| EFB1 | 34191 | 16459 | 10007 | 10917 | 13214 |

Example 4

Over-Expression of MIG3 in Yeast

To over-express MIG3, the promoter of endogenous MIG3 was swapped with the EFB1 promoter in an FG parent. The expected replacement of the MIG3 promoter by the EFB1 promoter was confirmed by PCR. The amino acid sequence of the MIG3 polypeptide is shown, below, as SEQ ID NO: 1:

MNYLRDRFPPDNDQRPFRCEICSRGFHRLEHKKRHVRTHTGEKPHKCTVQ

GCPKSFSRSDELKRHLRTHTKGVQRRRIKSKGSRKTVVNTATAAPTTFNE

-continued

NTGVSLTGIGQSKVPPILISVAQNCDDVNIRNTGNNNGIVETQAPAILVP

VINIPNDPHPIPSSLSTTSITSIASVYPSTSPFQYLKSGFPEDPASTPYV

HSSGSSLALGELSSNSSIFSKSRRNLAAMSGPDSLSSSKNQSSASLLSQT

SHPSKSFSRPPTDLSPLRRIMPSVNTGDMEISRTVSVSSSSSSLTSVTYD

DTAAKDMGMGIFFDRPPVTQKACRSNHKYKVNAVSRGRQHERAQFHISGD

DEDSNVHRQESRASNTSPNVSLPPIKSILRQIDNFNSAPSYFSK

The DNA sequence of the MIG3 coding region is shown, below, as SEQ ID NO: 2:

ATGAATTACCTGCGAGATAGATTTCCTCCGGATAATGACCAAAGACCCTT

TAGATGTGAAATTTGTTCACGAGGTTTCCACAGACTTGAACATAAAAAA

GGCACGTAAGAACGCACACTGGCGAGAAGCCTCACAAATGTACCGTTCAG

GGCTGTCCGAAAAGCTTCAGCCGAAGCGATGAACTAAAAAGACATTTGAG

GACACATACTAAAGGCGTCCAAAGGCGCAGAATAAAATCCAAGGGCTCGC

GAAAAACCGTTGTGAATACTGCTACCGCCGCCCCTACCACCTTCAATGAA

AACACTGGTGTTTCGCTCACGGGGATAGGTCAATCTAAAGTGCCACCTAT

TCTTATCTCCGTTGCTCAGAATTGCGATGACGTGAATATACGAAATACTG

GAAATAATAATGGCATTGTGGAGACACAGGCACCTGCAATTTTAGTGCCT

GTGATAAATATTCCAAATGACCCTCATCCGATTCCAAGTAGCCTCTCCAC

TACTTCTATCACCTCCATTGCATCAGTATATCCCTCTACTTCTCCATTCC

AGTACCTGAAAAGCGGGTTTCCTGAAGATCCTGCATCTACACCGTATGTA

CATTCGTCCGGAAGTTCTTTAGCCCTGGGTGAATTGTCTTCAAACTCCTC

TATATTTTCGAAATCTAGGAGGAATTTGGCCGCCATGAGTGGTCCTGATT

CTTTGAGTAGTTCTAAAAACCAATCCAGTGCTTCGCTTCTTTCTCAAACT

TCACATCCATCAAAGAGCTTTTCAAGACCGCCAACAGACTTAAGTCCTCT

GCGAAGAATCATGCCTTCTGTAAACACAGGAGACATGGAAATTTCAAGGA

CAGTATCCGTTTCGAGCAGTTCATCATCACTCACTTCTGTTACGTATGAT

GACACCGCGGCTAAAGACATGGGCATGGGAATATTTTTTGATAGGCCACC

TGTAACACAGAAAGCTTGCAGGAGCAATCATAAGTACAAGGTTAATGCTG

TTAGCAGAGGGAGACAACATGAAAGGGCACAATTTCATATATCTGGAGAT

GATGAGGACAGTAACGTTCACCGCCAAGAATCAAGAGCATCCAACACAAG

TCCCAATGTATCATTGCCTCCGATAAAGAGCATTTTGCGACAAATTGATA

ATTTCAACAGTGCTCCTTCTTACTTCAGTAAATAA

The DNA sequence of the EFB1 promoter is shown, below, as SEQ ID NO: 3:

GCAACACACGAGTATGTTGTACCTAAATCAATACCGACAGCTTTTGACAT

ATTATCTGTTATTTACTTGAATTTTTGTTTCTTGTAATACTTGATTACTT

TTCTTTTGATGTGCTTATCTTACAAATAGAGAAAATAAAACAACTTAAGT

AAGAATTGGGAAACGAAACTACAACTCAATCCCTTCTCGAAGATACATCA

ATCCACCCCTTATATAACCTTGAAGTCCTCGAAACGATCAGCTAATCTAA

ATGGCCCCCCTTCTTTTTGGGTTCTTTCTCTCCCTTTTGCCGCCGATGGA

-continued

ACGTTCTGGAAAAAGAAGAATAATTTAATTACTTTCTCAACTAAAATCTG

GAGAAAAAACGCAAATGACAGCTTCTAAACGTTCCGTGTGCTTTCTTTCT

AGAATGTTCTGGAAAGTTTACAACAATCCACAAGAACGAAAATGCCGTTG

ACAATGATGAAACCATCATCCACACACCGCGCACACGTGCTTTATTTCTT

TTTCTGAATTTTTTTTTTCCGCCATTTTCAACCAAGGAAATTTTTTTTCT

TAGGGCTCAGAACCTGCAGGTGAAGAAGCGCTTTAGAAATCAAAGCACAA

CGTAACAATTTGTCGACAACCGAGCCTTTGAAGAAAAAATTTTTCACATT

GTCGCCTCTAAATAAATAGTTTAAGGTTATCTACCCACTATATTTAGTTG

GTTCTTTTTTTTTTCCTTCTACTCTTTATCTTTTTACCTCATGCTTTCTA

CCTTTCAGCACTGAAGAGTCCAACCGAATATATACACACATA

Example 5

Alcohol Production Using Yeast that Over-Express MIG3

A yeast strain over-expressing MIG3 (FG-MIG3) and its corresponding parental strain (FG) were tested in a small vial assay, containing 5.6 g liquefact, as described in Example 1. Fermentations were performed at 32° C. for 55 hours. Samples from the end of fermentation were analyzed by HPLC. The results are summarized in Table 3.

TABLE 3

HPLC results from a small vial assay

| Strain | Glycerol (g/L) | Acetate (g/L) | Glucose (g/L) | Ethanol (g/L) | Acetate reduction (%) |
|---|---|---|---|---|---|
| FG | 13.89 | 1.29 | 0.86 | 145.35 | -0- |
| FG-MIG3 | 13.71 | 0.98 | 1.39 | 145.58 | ~24% |

Over-expression of MIG3 resulted in a decrease in acetate production of about 24% without a negative impact in ethanol production. These results demonstrate that MIG3 over-expression is beneficial for acetate reduction during yeast fermentation for ethanol production.

Example 6

Further Promoter Selection for Increased Expression of MIG1 and MIG2

Encouraged by the significant acetate reduction in cells over-expressing MIG3, additional experiments were performed to determine if the use of a weaker promoter than EFB1 (table 2) could produce similar acetate reduction by over-expressing MIG1 and MIG2. Similar to Example 2, RNA-Seq analyses were performed using FERMAX™ Gold yeast over-expressing MIG1, MIG2 or SUI3, which encodes the 0 subunit of eukaryotic initiation factor 2 (eIF-2). The results of the RNA-Seq analyses are summarized in Table 4. As before, levels are expressed as reads per kilobase ten million transcripts (RPK10M). The data confirm that MIG1 and MIG2 are expressed at low levels during fermentation in the FERMAX™ Gold strain.

TABLE 4

RNA-Seq analyses of MIG1, MIG2 and SUI3 in FERMAX ™ Gold during fermentation process

| | FG Strain | | |
|---|---|---|---|
| Time | MIG1 | MIG2 | SUI3 |
| 12 hr | 473 | 359 | 3325 |
| 24 hr | 468 | 618 | 2761 |
| 36 hr | 242 | 238 | 4144 |
| 48 hr | 294 | 282 | 3370 |

In contrast to very weak expression of MIG1 and MIG2, SUI3 was expressed at levels about 5 to 20 times higher than the MIG1 or MIG2 throughout the fermentation process. Accordingly, the SUI3 promoter was selected to drive the over-expression of MIG1 and MIG2.

Example 7

Preparation of MIG1 and MIG2 Expression Cassettes

The MIG1 gene (YGL035C) and the MIG2 gene (YGL209W) of *S. cerevisiae* were codon optimized and then synthesized to generate MIG1s (SEQ ID: 4 and 5) and MIG2s (SEQ ID: 6 and 7), respectively. The SUI3 promoter (YPL237W locus; SEQ ID NO: 8) was individually linked to the MIG1 or MIG2, and the GPD1 terminator (YDL022W locus; SEQ ID NO: 9) to generate the SUI3Pro::MIG1s::Gpd1Ter and SUI3pro::MIG2s::Gpd1Ter expression cassettes. Both expression cassettes were separately introduced into FERMAX™ Gold yeast downstream of the RPA190 locus (YOR341W). The expected insertion of the MIG1s and MIG2s expression cassette in the parental strains was confirmed by PCR.

The DNA sequence of codon optimized MIG1 coding region (MIG1s) is shown, below, as SEQ ID NO: 4:

ATGCAATCTCCATACCCAATGACTCAAGTTTCCAACGTTGACGATGGTTC
TTTGTTGAAGGAATCCAAGAGCAAATCCAAGGTTGCTGCCAAGTCTGAAG
CTCCAAGACCTCACGCTTGTCCAATCTGTCACAGAGCTTTTCACAGATTG
GAACACCAAACCAGACACATGCGTATTCACACTGGTGAAAAGCCACATGC
TTGTGACTTTCCAGGTTGTGTCAAGAGATTTTCCAGAAGCGACGAATTGA
CCAGACACAGGCGTATTCACACCAACTCTCACCCAAGAGGCAAGAGAGGC
AGAAAGAAGAAAGTCGTTGGTTCTCCAATCAACAGTGCTAGCTCCTCTGC
TACCTCTATTCCAGACTTGAATACTGCCAACTTTTCTCCTCCATTGCCAC
AGCAACACTTGTCTCCATTGATTCCAATCGCCATTGCTCCCAAGGAAAAC
TCCAGTCGTTCTTCCACCAGAAAGGGTCGTAAGACCAAATTCGAGATTGG
CGAATCTGGTGGCAACGATCCATACATGGTCTCCTCTCCAAAGACTATGG
CCAAGATTCCAGTTTCTGTCAAGCCTCCACCCTCTTTGGCTCTAAACAAT
ATGAACTACCAAACTTCATCTGCTTCCACTGCCTTATCTTCATTGTCCAA
CAGTCACTCTGGTTCCAGATTGAAGCTGAACGCTTTGTCTTCCTTACAAA
TGATGACTCCAATTGCCAGCTCTGCTCCAAGAACCGTCTTCATCGATGGT
CCAGAACAAAAGCAGTTGCAACAACAGCAAAACTCCTTGTCTCCAAGATA

-continued

CTCCAACACCGTCATTCTACCAAGACCACGTTCCTTGACCGACTTTCAAG
GTTTGAACAATGCCAACCCAAACAACAATGGTTCTTTGAGGGCTCAAACT
CAAAGTTCCGTTCAATTGAAGAGACCATCCTCTGTCTTATCCTTGAACGA
CCTATTGGTTGGTCAAAGAAACACCAACGAATCCGATTCTGACTTTACCA
CTGGTGGCGAAGACGAGGAAGACGGTTTGAAGGATCCATCCAACTCTAGC
ATCGACAACTTGGAACAAGACTACTTGCAAGAACAGTCCAGAAAGAAATC
CAAGACTTCTACTCCAACCACTATGTTGTCCAGATCTACATCTGGTACCA
ACTTACACACTTTGGGCTACGTCATGAACCAGAACCACTTGCACTTTTCC
TCTTCAAGTCCAGACTTTCAGAAGGAATTGAACAATAGACTATTGAACGT
TCAACAACAGCAACAGGAACAACATACCTTGCTACAATCTCAAAACACTT
CCAACCAATCTCAAAATCAAAACCAGAATCAAATGATGGCTTCATCCAGT
TCTTTGTCCACCACTCCATTGTTACTATCTCCAAGAGTCAACATGATCAA
CACTGCTATTTCTACCCAACAGACTCCAATTTCTCAATCCGATTCTCAAG
TTCAAGAGTTGGAAACCTTGCCACCTATCAGATCTTTACCATTGCCCTTT
CCACACATGGACTAA

The amino acid sequence of the MIG1 polypeptide is shown, below, as SEQ ID NO: 5:

MQSPYPMTQVSNVDDGSLLKESKSKSKVAAKSEAPRPHACPICHRAFHRL
EHQTRHMRIHTGEKPHACDFPGCVKRFSRSDELTRHRRIHTNSHPRGKRG
RKKKVVGSPINSASSSATSIPDLNTANFSPPLPQQHLSPLIPIAIAPKEN
SSRSSTRKGRKTKFEIGESGGNDPYMVSSPKTMAKIPVSVKPPPSLALNN
MNYQTSSASTALSSLSNSHSGSRLKLNALSSLQMMTPIASSAPRTVFIDG
PEQKQLQQQQNSLSPRYSNTVILPRPRSLTDFQGLNNANPNNNGSLRAQT
QSSVQLKRPSSVLSLNDLLVGQRNTNESDSDFTTGGEDEEDGLKDPSNSS
IDNLEQDYLQEQSRKKSKTSTPTTMLSRSTSGTNLHTLGYVMNQNHLHFS
SSSPDFQKELNNRLLNVQQQQQEQHTLLQSQNTSNQSQNQNQNQMMASSS
SLSTTPLLLSPRVNMINTAISTQQTPISQSDSQVQELETLPPIRSLPLPF
PHMD

The DNA sequence of codon optimized MIG2 coding region (MIG2s) is shown, below, as SEQ ID NO: 6:

ATGCCAAAGAAGCAAACCAACTTTCCAGTTGACAACGAAAACAGACCATT
CAGATGTGATACCTGTCACAGAGGTTTTCACAGATTGGAACACAAGAAAC
GTCACTTGAGAACTCATACAGGTGAAAAGCCACACCATTGTGCCTTTCCA
GGTTGTGGCAAGAGCTTTTCCAGATCTGACGAATTGAAGAGACATATGAG
AACTCACACTGGTCAATCTCAAAGGCGTTTGAAAAAGGCTTCCGTTCAAA
AGCAGGAGTTCTTGACCGTCTCTGGCATTCCAACCATTGCTTCTGGTGTT
ATGATCCACCAACCAATTCCACAAGTCTTGCCAGCCAACATGGCTATCAA
CGTTCAAGCCGTCAATGGTGGCAACATCATTCACGCTCCCAACGCTGTTC
ATCCAATGGTCATTCCAATCATGGCTCAACCAGCTCCTATTCACGCTTCT
GCTGCCTCCTTTCAACCAGCTACCTCTCCTATGCCAATCTCTACATACAC

-continued

TCCAGTTCCATCTCAATCCTTTACCTCTTTTCAATCCTCTATTGGTTCCA
TCCAATCCAACAGTGATGTCTCTTCCATCTTCTCAAACATGAATGTCAGA
GTCAACACTCCAAGATCTGTTCCAAACTCACCCAACGACGGTTACTTACA
CCAACAGCACATTCCACAACAGTACCAACACCAAACTGCTTCTCCATCTG
TTGCCAAGCAACAGAAGACCTTTGCTCACTCCTTGGCTTCTGCCTTGTCC
ACCTTACAAAAGAGAACTCCAGTCAGTGCTCCTTCTACCACTATCGAATC
TCCATCCTCTCCAAGTGACTCCAGTCACACTTCTGCTTCCAGCAGTGCTA
TCTCTTTGCCATTCTCCAATGCTCCATCTCAACTAGCTGTTGCCAAGGAG
TTGGAATCCGTTTACTTGGATTCCAACAGATACACTACCAAGACTCGTAG
AGAAAGAGCCAAGTTCGAAATTCCAGAAGAGCAAGAAGAAGACACCAACA
ATTCTTCCTCAGGTTCCAACGAAGAAGAGCACGAATCTCTAGATCACGAA
TCTTCCAAGAGCAGAAAGAAACTATCTGGTGTCAAGTTGCCACCTGTCAG
AAACTTATTGAAGCAAATCGACGTTTTCAACGGTCCAAAGAGAGTTTAA

The amino acid sequence of the MIG2 polypeptide is shown, below, as SEQ ID NO: 7:

MPKKQTNFPVDNENRPFRCDTCHRGPHRLBHKKRHLRTHTGEKPHHCAPP
GCGKSFSRSDEIKRHMRTHTGQSQRRLKKASVQKQEFLTVSGIPTIASGV
MIHQPIPQVLPANMAINVQAVNGGNIIHAPNAVHPMVIPIMAQPAPIHAS
AASFQPATSPMPISTYTPVPSQSFTSFQSSIGSIQSNSDVSSIFSNMNVR
VNTPRSVPNSPNDGYLHQQHIPQQYQHQTASPSVAKQQKTFAHSLASALS
TLQKRTPVSAPSTTIESPSSPSDSSHTSASSSAISLPFSNAPSQLAVAKE
LESVYLDSNRYTTKTRRERAKFEIPEEQEEDTNNSSSGSNEEEHESLDHE
SSKSRKKLSGVKLPPVRNLLKQIDVFNGPKRV

The DNA sequence of SUI3 promoter shown, below, as SEQ ID NO: 8:

CTTTTGTTAATGAGGTGAACAAAACAGGCAACACGGCTTTACATTGGGCG
TCGTTGAATGGCAAATTAGACGTGGTCAAGCTACTGTGTGATGAATATGA
GGCAGACCCCTTTATTAGAAACAAATTCGGCCACGATGCTATCTTTGAGG
CCGAGAACAGCGGGAAGGAAGAAGTGGAAACATACTTTTTGAAGAAGTAT
GATGTCGAACCTGAAGATGATGAAGAAGACACACAAACTGAGGGCAAGAA
TTCGGTCCAAATCACAAAGGGTACAGAAATTGAACAAGTCACCAAGGAAG
CCACCGAGGCTTTAAGAGAAGAAACCGAGAAACTGAATATAAATAAAGAC
TAAAGTAAAGAGCTTGTTTTCTTCGTGGAATAAAAGCCGTAATATCCATT
GAGCATGATATTTTATTTCTTGGTACCGGAGAAGATAAAAGGATGGAACC

-continued

AGCAGAAATGCATTAATAAATACAAAAAATTTAGAAAAGAGTTACAGTAA
TAATGTATATTTCTCTCACAAACTAAGTAACCGCTTCAAAAGCGTATATT
TTGAATGCATTGAACTTTCCATTTCATTACCCGCAGAGCCGGAGTCCTCA
TCAACGACGGAGTGAAAAATTTTGTAATTGCGAGAAAAAGTGAAATTGAT
GGAAAAAAAGAAAAAGAAAGTAGAAGAAGACATTATAAGAGAGACTAGGA
AACTTCTTGCACATCAACCGAAAAGCGCCTAGGCAACCAGTCATATAAAA
GCACGCACGAG

The DNA sequence of GPD1 terminator region shown, below, as SEQ ID NO: 9:

ATTTATTGGAGAAAGATAACATATCATACTTTCCCCCACTTTTTTCGAGG
CTCTTCTATATCATATTCATAAATTAGCATTATGTCATTTCTCATAACTA
CTTTATCACGTTAGAAATTACTTATTATTATTAAATTAATACAAAATTTA
GTAACCAAATAAATATAAATAAATATGTATATTTGAATTTTAAAAAAAAA
ATCCTATAGAGCAAAAGGATTTTCCATTATAATATTAGCTGTACACCTCT
TCCGCATTTTTTGAGGGTGGTTACAACACCACTCATTCAGAGGCTGTCGG
CACAGTTGCTTCTAGCATCTGGCGTCCGTATGTATGGGTGTATTTTAAAT
AA

Example 8

Ethanol and Acetate Production by MIG1 or MIG2 Over-Expressing Yeast

One each of a PCR-confirmed strain over-expressing MIG1 or MIG2 under control of the SUI1 promoter, along with the FG parental strain were tested in an Ankom assay as described in Example 1. Fermentations were performed at 32° C. for 55 hours. Samples from the end of fermentation were analyzed by HPLC analyses. The results are summarized in Table 5.

TABLE 5

HPLC results from FG and FG over-express MIG1 or MIG2 with SUI3 promoter

| Strain | Glucose (g/L) | Glycerol (g/L) | Acetate (g/L) | Ethanol (g/L) | Acetate Reduction | Glycerol Reduction |
|---|---|---|---|---|---|---|
| FG-MIG1 | 1.56 | 14.15 | 1.02 | 141.25 | 15% | 3.8% |
| FG-MIG2 | 3.92 | 13.83 | 0.76 | 141.25 | 36.4% | 6.0% |
| FG Parent | 1.56 | 14.72 | 1.20 | 141.30 | | |

The results demonstrate that over-expression of MIG1 or MIG2 with SUI3 promoter resulted in about 15% or 36% reduction of acetate and 3.8% or 6% reduction of glycerol, respectively; without negative effect on ethanol yield.

What is claimed is:

1. A method for decreasing the production of acetate from yeast cells grown on a carbohydrate substrate, comprising: producing modified yeast cells by introducing into parental yeast cells a genetic alteration that increases the production of MIG transcription regulator polypeptides compared to the amount produced by the parental yeast cells;

wherein the genetic alteration comprises one or more of:

(a) introducing into the parental yeast cells an expression cassette for producing the MIG transcription regulator polypeptide; or (b) modifying the MIG transcription regulator polypeptide promoter to increase expression of the MIG transcription regulator polypeptide;

wherein the MIG transcription regulator polypeptide is a MIG3 transcription regulator polypeptide comprising an amino acid sequence having at least 80% sequence identity to the amino acid sequence set forth by SEQ ID NO: 1; and wherein the modified yeast cells produce during fermentation of a carbohydrate substrate a decreased amount of acetate compared to the amount of acetate produced by the otherwise identical parental yeast cells lacking the genetic alteration under identical fermentation conditions.

2. The method of claim 1, wherein the decrease in acetate production is at least 5%, at least 10%, at least 15%, at least 20%, at least 25%, at least 30%, at least 35%, at least 40%, at least 50%, at least 60%, or more.

3. The method of claim 1, wherein the MIG transcription regulator polypeptides are over-expressed by at least 20%, at least 30%, at least 40%, at least 50%, at least 70%, at least 100%, at least 150%, at least 200%, at least 500%, at least 1,000%, at least 2,000%, or more, compared to the amount of the MIG transcription regulator polypeptides produced by otherwise identical parental yeast cells grown under the same conditions.

4. The method of claim 1, wherein mRNA of the MIG transcription regulator is over-expressed by at least 2-fold, at least 5-fold, at least 10-fold, at least 20-fold, at least 50-fold, at least 100-fold or more, compared to the amount of mRNA of the MIG transcription regulator produced by otherwise identical parental yeast cells grown under the same conditions.

5. The method of claim 1, wherein the modified yeast cells further comprise one or more genes of the phosphoketolase pathway selected from the group consisting of phosphoketolase, phosphotransacetylase and acetylating acetyl dehydrogenase.

6. The method of claim 1, wherein the modified yeast cells further comprise an exogenous gene encoding a carbohydrate processing enzyme and/or other polypeptide, wherein the carbohydrate processing enzyme and/or other polypeptide is selected from the group consisting of a dehydrogenase, a transketolase, a phosphoketolase, a transaldolase, an epimerase, a phytase, a xylanase, a β-glucanase, a phosphatase, a protease, an a-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase.

7. The method of claim 1, wherein the modified yeast cells further comprise an alteration in the glycerol pathway, wherein the alteration comprises reducing or eliminating endogenous GPD1 and/or GPD2 activity, and/or overexpressing glycerol dehydrogenase and/or dihydroxyacetone kinase.

8. The method of claim 1, wherein the modified yeast cells are of a *Saccharomyces* spp.

9. The method of claim 1, wherein the modified yeast cells further comprise an alteration in the acetyl-CoA pathway, wherein the alteration comprises expressing a heterologous acetyl-CoA synthase gene.

10. The method of claim 1, further comprising introducing into the parental yeast cells a genetic alteration that increases the production of MIG2 transcription regulator polypeptides compared to the amount produced by the parental yeast cells, wherein the genetic alteration comprises one or more of:

(a) introducing into the parental yeast cells an expression cassette for producing the MIG2 transcription regulator polypeptide; or (b) modifying the MIG2 transcription regulator polypeptide promoter to increase expression of the MIG2 transcription regulator polypeptide.

11. The method of claim 10, wherein the MIG2 transcription regulator polypeptides comprise an amino acid sequence having at least 80% sequence identity to the amino acid sequence set forth by SEQ ID NO: 7.

12. The method of claim 1, wherein the carbohydrate substrate is corn starch.

* * * * *

SEQUENCE LISTING

<160> NUMBER OF SEQ ID NOS: 9

<210> SEQ ID NO 1
<211> LENGTH: 394
<212> TYPE: PRT

-continued

<213> ORGANISM: Saccharomyces cerevisiae

<400> SEQUENCE: 1

Met Asn Tyr Leu Arg Asp Arg Phe Pro Pro Asp Asn Asp Gln Arg Pro
1 5 10 15

Phe Arg Cys Glu Ile Cys Ser Arg Gly Phe His Arg Leu Glu His Lys
20 25 30

Lys Arg His Val Arg Thr His Thr Gly Glu Lys Pro His Lys Cys Thr
35 40 45

Val Gln Gly Cys Pro Lys Ser Phe Ser Arg Ser Asp Glu Leu Lys Arg
50 55 60

His Leu Arg Thr His Thr Lys Gly Val Gln Arg Arg Arg Ile Lys Ser
65 70 75 80

Lys Gly Ser Arg Lys Thr Val Val Asn Thr Ala Thr Ala Ala Pro Thr
85 90 95

Thr Phe Asn Glu Asn Thr Gly Val Ser Leu Thr Gly Ile Gly Gln Ser
100 105 110

Lys Val Pro Pro Ile Leu Ile Ser Val Ala Gln Asn Cys Asp Asp Val
115 120 125

Asn Ile Arg Asn Thr Gly Asn Asn Asn Gly Ile Val Glu Thr Gln Ala
130 135 140

Pro Ala Ile Leu Val Pro Val Ile Asn Ile Pro Asn Asp Pro His Pro
145 150 155 160

Ile Pro Ser Ser Leu Ser Thr Thr Ser Ile Thr Ser Ile Ala Ser Val
165 170 175

Tyr Pro Ser Thr Ser Pro Phe Gln Tyr Leu Lys Ser Gly Phe Pro Glu
180 185 190

Asp Pro Ala Ser Thr Pro Tyr Val His Ser Ser Gly Ser Ser Leu Ala
195 200 205

Leu Gly Glu Leu Ser Ser Asn Ser Ser Ile Phe Ser Lys Ser Arg Arg
210 215 220

Asn Leu Ala Ala Met Ser Gly Pro Asp Ser Leu Ser Ser Ser Lys Asn
225 230 235 240

Gln Ser Ser Ala Ser Leu Leu Ser Gln Thr Ser His Pro Ser Lys Ser
245 250 255

Phe Ser Arg Pro Pro Thr Asp Leu Ser Pro Leu Arg Arg Ile Met Pro
260 265 270

Ser Val Asn Thr Gly Asp Met Glu Ile Ser Arg Thr Val Ser Val Ser
275 280 285

Ser Ser Ser Ser Ser Leu Thr Ser Val Thr Tyr Asp Asp Thr Ala Ala
290 295 300

Lys Asp Met Gly Met Gly Ile Phe Phe Asp Arg Pro Pro Val Thr Gln
305 310 315 320

Lys Ala Cys Arg Ser Asn His Lys Tyr Lys Val Asn Ala Val Ser Arg
325 330 335

Gly Arg Gln His Glu Arg Ala Gln Phe His Ile Ser Gly Asp Asp Glu
340 345 350

Asp Ser Asn Val His Arg Gln Glu Ser Arg Ala Ser Asn Thr Ser Pro
355 360 365

Asn Val Ser Leu Pro Pro Ile Lys Ser Ile Leu Arg Gln Ile Asp Asn
370 375 380

Phe Asn Ser Ala Pro Ser Tyr Phe Ser Lys
385 390

<210> SEQ ID NO 2
<211> LENGTH: 1185
<212> TYPE: DNA
<213> ORGANISM: Saccharomyces cerevisiae

<400> SEQUENCE: 2
atgaattacc tgcgagatag atttcctccg gataatgacc aaagaccctt tagatgtgaa 60
atttgttcac gaggtttcca cagacttgaa cataaaaaaa ggcacgtaag aacgcacact 120
ggcgagaagc ctcacaaatg taccgttcag ggctgtccga aaagcttcag ccgaagcgat 180
gaactaaaaa gacatttgag gacacatact aaaggcgtcc aaaggcgcag aataaaatcc 240
aagggctcgc gaaaaaccgt tgtgaatact gctaccgccg cccctaccac cttcaatgaa 300
aacactggtg tttcgctcac ggggataggt caatctaaag tgccacctat tcttatctcc 360
gttgctcaga attgcgatga cgtgaatata cgaaatactg gaaataataa tggcattgtg 420
gagacacagg cacctgcaat tttagtgcct gtgataaata ttccaaatga ccctcatccg 480
attccaagta gcctctccac tacttctatc acctccattg catcagtata tccctctact 540
tctccattcc agtacctgaa aagcgggttt cctgaagatc ctgcatctac accgtatgta 600
cattcgtccg gaagttcttt agccctgggt gaattgtctt caaactcctc tatattttcg 660
aaatctagga ggaatttggc cgccatgagt ggtcctgatt ctttgagtag ttctaaaaac 720
caatccagtg cttcgcttct ttctcaaact tcacatccat caaagagctt ttcaagaccg 780
ccaacagact taagtcctct gcgaagaatc atgccttctg taaacacagg agacatggaa 840
atttcaagga cagtatccgt ttcgagcagt tcatcatcac tcacttctgt tacgtatgat 900
gacaccgcgg ctaaagacat gggcatggga atatttttg ataggccacc tgtaacacag 960
aaagcttgca ggagcaatca taagtacaag gttaatgctg ttagcagagg gagacaacat 1020
gaaagggcac aatttcatat atctggagat gatgaggaca gtaacgttca ccgccaagaa 1080
tcaagagcat ccaacacaag tcccaatgta tcattgcctc cgataaagag cattttgcga 1140
caaattgata atttcaacag tgctccttct tacttcagta aataa 1185

<210> SEQ ID NO 3
<211> LENGTH: 792
<212> TYPE: DNA
<213> ORGANISM: Artificial Sequence
<220> FEATURE:
<223> OTHER INFORMATION: Synthetic DNA

<400> SEQUENCE: 3
gcaacacacg agtatgttgt acctaaatca ataccgacag cttttgacat attatctgtt 60
atttacttga atttttgttt cttgtaatac ttgattactt ttcttttgat gtgcttatct 120
tacaaataga gaaaataaaa caacttaagt aagaattggg aaacgaaact acaactcaat 180
cccttctcga agatacatca atccacccct tatataacct tgaagtcctc gaaacgatca 240
gctaatctaa atggcccccc ttcttttttgg gttctttctc tccctttttgc cgccgatgga 300 acgttctgga aaaagaagaa taatttaatt actttctcaa ctaaaatctg gagaaaaaac 360
gcaaatgaca gcttctaaac gttccgtgtg ctttctttct agaatgttct ggaaagttta 420
caacaatcca caagaacgaa aatgccgttg acaatgatga aaccatcatc cacacaccgc 480
gcacacgtgc tttatttctt tttctgaatt ttttttttcc gccattttca accaaggaaa 540 tttttttttct tagggctcag aacctgcagg tgaagaagcg ctttagaaat caaagcacaa 600
cgtaacaatt tgtcgacaac cgagcctttg aagaaaaaat ttttcacatt gtcgcctcta 660

```
aataaatagt ttaaggttat ctacccacta tatttagttg gttctttttt ttttccttct    720

actctttatc tttttacctc atgctttcta cctttcagca ctgaagagtc caaccgaata    780

tatacacaca ta                                                        792
```

<210> SEQ ID NO 4
<211> LENGTH: 1515
<212> TYPE: DNA
<213> ORGANISM: Artificial Sequence
<220> FEATURE:
<223> OTHER INFORMATION: Synthetic DNA

<400> SEQUENCE: 4

```
atgcaatctc catacccaat gactcaagtt tccaacgttg acgatggttc tttgttgaag      60

gaatccaaga gcaaatccaa ggttgctgcc aagtctgaag ctccaagacc tcacgcttgt     120

ccaatctgtc acagagcttt tcacagattg gaacaccaaa ccagacacat gcgtattcac     180

actggtgaaa agccacatgc ttgtgacttt ccaggttgtg tcaagagatt ttccagaagc     240

gacgaattga ccagacacag gcgtattcac accaactctc acccaagagg caagagaggc     300

agaaagaaga aagtcgttgg ttctccaatc aacagtgcta gctcctctgc tacctctatt     360

ccagacttga atactgccaa cttttctcct ccattgccac agcaacactt gtctccattg     420

attccaatcg ccattgctcc caaggaaaac tccagtcgtt cttccaccag aaagggtcgt     480

aagaccaaat tcgagattgg cgaatctggt ggcaacgatc catacatggt ctcctctcca     540

aagactatgg ccaagattcc agtttctgtc aagcctccac cctctttggc tctaaacaat     600

atgaactacc aaacttcatc tgcttccact gccttatctt cattgtccaa cagtcactct     660

ggttccagat tgaagctgaa cgctttgtct tccttacaaa tgatgactcc aattgccagc     720

tctgctccaa gaaccgtctt catcgatggt ccagaacaaa agcagttgca acaacagcaa     780

aactccttgt ctccaagata ctccaacacc gtcattctac caagaccacg ttccttgacc     840

gactttcaag gtttgaacaa tgccaaccca aacaacaatg gttctttgag ggctcaaact     900

caaagttccg ttcaattgaa gagaccatcc tctgtcttat ccttgaacga cctattggtt     960

ggtcaaagaa acaccaacga atccgattct gactttacca ctggtggcga agacgaggaa    1020

gacggtttga aggatccatc caactctagc atcgacaact tggaacaaga ctacttgcaa    1080

gaacagtcca gaaagaaatc caagacttct actccaacca ctatgttgtc cagatctaca    1140

tctggtacca acttacacac tttgggctac gtcatgaacc agaaccactt gcacttttcc    1200

tcttcaagtc cagactttca gaaggaattg aacaatagac tattgaacgt tcaacaacag    1260

caacaggaac aacatacctt gctacaatct caaaacactt ccaaccaatc tcaaaatcaa    1320

aaccagaatc aaatgatggc ttcatccagt tctttgtcca ccactccatt gttactatct    1380

ccaagagtca acatgatcaa cactgctatt tctacccaac agactccaat ttctcaatcc    1440

gattctcaag ttcaagagtt ggaaaccttg ccacctatca gatctttacc attgcccttt    1500

ccacacatgg actaa                                                     1515
```

<210> SEQ ID NO 5
<211> LENGTH: 504
<212> TYPE: PRT
<213> ORGANISM: Saccharomyces cerevisiae

<400> SEQUENCE: 5

```
Met Gln Ser Pro Tyr Pro Met Thr Gln Val Ser Asn Val Asp Asp Gly
1               5                   10                  15
```

-continued

```
Ser Leu Leu Lys Glu Ser Lys Ser Lys Ser Lys Val Ala Ala Lys Ser
            20                  25                  30

Glu Ala Pro Arg Pro His Ala Cys Pro Ile Cys His Arg Ala Phe His
        35                  40                  45

Arg Leu Glu His Gln Thr Arg His Met Arg Ile His Thr Gly Glu Lys
    50                  55                  60

Pro His Ala Cys Asp Phe Pro Gly Cys Val Lys Arg Phe Ser Arg Ser
65                  70                  75                  80

Asp Glu Leu Thr Arg His Arg Arg Ile His Thr Asn Ser His Pro Arg
                85                  90                  95

Gly Lys Arg Gly Arg Lys Lys Lys Val Val Gly Ser Pro Ile Asn Ser
            100                 105                 110

Ala Ser Ser Ser Ala Thr Ser Ile Pro Asp Leu Asn Thr Ala Asn Phe
        115                 120                 125

Ser Pro Pro Leu Pro Gln Gln His Leu Ser Pro Leu Ile Pro Ile Ala
    130                 135                 140

Ile Ala Pro Lys Glu Asn Ser Ser Arg Ser Ser Thr Arg Lys Gly Arg
145                 150                 155                 160

Lys Thr Lys Phe Glu Ile Gly Glu Ser Gly Gly Asn Asp Pro Tyr Met
                165                 170                 175

Val Ser Ser Pro Lys Thr Met Ala Lys Ile Pro Val Ser Val Lys Pro
            180                 185                 190

Pro Pro Ser Leu Ala Leu Asn Asn Met Asn Tyr Gln Thr Ser Ser Ala
        195                 200                 205

Ser Thr Ala Leu Ser Ser Leu Ser Asn Ser His Ser Gly Ser Arg Leu
    210                 215                 220

Lys Leu Asn Ala Leu Ser Ser Leu Gln Met Met Thr Pro Ile Ala Ser
225                 230                 235                 240

Ser Ala Pro Arg Thr Val Phe Ile Asp Gly Pro Glu Gln Lys Gln Leu
                245                 250                 255

Gln Gln Gln Gln Asn Ser Leu Ser Pro Arg Tyr Ser Asn Thr Val Ile
            260                 265                 270

Leu Pro Arg Pro Arg Ser Leu Thr Asp Phe Gln Gly Leu Asn Asn Ala
        275                 280                 285

Asn Pro Asn Asn Asn Gly Ser Leu Arg Ala Gln Thr Gln Ser Ser Val
    290                 295                 300

Gln Leu Lys Arg Pro Ser Ser Val Leu Ser Leu Asn Asp Leu Leu Val
305                 310                 315                 320

Gly Gln Arg Asn Thr Asn Glu Ser Asp Ser Asp Phe Thr Thr Gly Gly
                325                 330                 335

Glu Asp Glu Glu Asp Gly Leu Lys Asp Pro Ser Asn Ser Ser Ile Asp
            340                 345                 350

Asn Leu Glu Gln Asp Tyr Leu Gln Glu Gln Ser Arg Lys Lys Ser Lys
        355                 360                 365

Thr Ser Thr Pro Thr Thr Met Leu Ser Arg Ser Thr Ser Gly Thr Asn
    370                 375                 380

Leu His Thr Leu Gly Tyr Val Met Asn Gln Asn His Leu His Phe Ser
385                 390                 395                 400

Ser Ser Ser Pro Asp Phe Gln Lys Glu Leu Asn Asn Arg Leu Leu Asn
                405                 410                 415

Val Gln Gln Gln Gln Gln Glu Gln His Thr Leu Leu Gln Ser Gln Asn
            420                 425                 430
```

-continued

```
Thr Ser Asn Gln Ser Gln Asn Gln Asn Gln Asn Gln Met Met Ala Ser
        435                 440                 445

Ser Ser Ser Leu Ser Thr Thr Pro Leu Leu Leu Ser Pro Arg Val Asn
    450                 455                 460

Met Ile Asn Thr Ala Ile Ser Thr Gln Gln Thr Pro Ile Ser Gln Ser
465                 470                 475                 480

Asp Ser Gln Val Gln Glu Leu Glu Thr Leu Pro Pro Ile Arg Ser Leu
                485                 490                 495

Pro Leu Pro Phe Pro His Met Asp
            500


<210> SEQ ID NO 6
<211> LENGTH: 1149
<212> TYPE: DNA
<213> ORGANISM: Saccharomyces cerevisiae

<400> SEQUENCE: 6

atgccaaaga agcaaaccaa ctttccagtt gacaacgaaa acagaccatt cagatgtgat      60

acctgtcaca gaggttttca cagattggaa cacaagaaac gtcacttgag aactcataca     120

ggtgaaaagc cacaccattg tgcctttcca ggttgtggca agagcttttc cagatctgac     180

gaattgaaga gacatatgag aactcacact ggtcaatctc aaaggcgttt gaaaaaggct     240

tccgttcaaa agcaggagtt cttgaccgtc tctggcattc caaccattgc ttctggtgtt     300

atgatccacc aaccaattcc acaagtcttg ccagccaaca tggctatcaa cgttcaagcc     360

gtcaatggtg gcaacatcat tcacgctccc aacgctgttc atccaatggt cattccaatc     420

atggctcaac cagctcctat tcacgcttct gctgcctcct ttcaaccagc tacctctcct     480

atgccaatct ctacatacac tccagttcca tctcaatcct ttacctcttt tcaatcctct     540

attggttcca tccaatccaa cagtgatgtc tcttccatct tctcaaacat gaatgtcaga     600

gtcaacactc caagatctgt tccaaactca cccaacgacg gttacttaca ccaacagcac     660

attccacaac agtaccaaca ccaaactgct tctccatctg ttgccaagca acagaagacc     720

tttgctcact ccttggcttc tgccttgtcc accttacaaa agagaactcc agtcagtgct     780

ccttctacca ctatcgaatc tccatcctct ccaagtgact ccagtcacac ttctgcttcc     840

agcagtgcta tctctttgcc attctccaat gctccatctc aactagctgt tgccaaggag     900

ttggaatccg tttacttgga ttccaacaga tacactacca agactcgtag agaaagagcc     960

aagttcgaaa ttccagaaga gcaagaagaa gacaccaaca attcttcctc aggttccaac    1020

gaagaagagc acgaatctct agatcacgaa tcttccaaga gcagaaagaa actatctggt    1080

gtcaagttgc cacctgtcag aaacttattg aagcaaatcg acgttttcaa cggtccaaag    1140

agagtttaa                                                            1149


<210> SEQ ID NO 7
<211> LENGTH: 382
<212> TYPE: PRT
<213> ORGANISM: Saccharomyces cerevisiae

<400> SEQUENCE: 7

Met Pro Lys Lys Gln Thr Asn Phe Pro Val Asp Asn Glu Asn Arg Pro
1               5                   10                  15

Phe Arg Cys Asp Thr Cys His Arg Gly Phe His Arg Leu Glu His Lys
            20                  25                  30

Lys Arg His Leu Arg Thr His Thr Gly Glu Lys Pro His His Cys Ala
        35                  40                  45
```

```
Phe Pro Gly Cys Gly Lys Ser Phe Ser Arg Ser Asp Glu Leu Lys Arg
    50                  55                  60

His Met Arg Thr His Thr Gly Gln Ser Gln Arg Arg Leu Lys Lys Ala
65                  70                  75                  80

Ser Val Gln Lys Gln Glu Phe Leu Thr Val Ser Gly Ile Pro Thr Ile
                85                  90                  95

Ala Ser Gly Val Met Ile His Gln Pro Ile Pro Gln Val Leu Pro Ala
            100                 105                 110

Asn Met Ala Ile Asn Val Gln Ala Val Asn Gly Gly Asn Ile Ile His
        115                 120                 125

Ala Pro Asn Ala Val His Pro Met Val Ile Pro Ile Met Ala Gln Pro
    130                 135                 140

Ala Pro Ile His Ala Ser Ala Ala Ser Phe Gln Pro Ala Thr Ser Pro
145                 150                 155                 160

Met Pro Ile Ser Thr Tyr Thr Pro Val Pro Ser Gln Ser Phe Thr Ser
                165                 170                 175

Phe Gln Ser Ser Ile Gly Ser Ile Gln Ser Asn Ser Asp Val Ser Ser
            180                 185                 190

Ile Phe Ser Asn Met Asn Val Arg Val Asn Thr Pro Arg Ser Val Pro
        195                 200                 205

Asn Ser Pro Asn Asp Gly Tyr Leu His Gln Gln His Ile Pro Gln Gln
    210                 215                 220

Tyr Gln His Gln Thr Ala Ser Pro Ser Val Ala Lys Gln Gln Lys Thr
225                 230                 235                 240

Phe Ala His Ser Leu Ala Ser Ala Leu Ser Thr Leu Gln Lys Arg Thr
                245                 250                 255

Pro Val Ser Ala Pro Ser Thr Thr Ile Glu Ser Pro Ser Ser Pro Ser
            260                 265                 270

Asp Ser Ser His Thr Ser Ala Ser Ser Ser Ala Ile Ser Leu Pro Phe
        275                 280                 285

Ser Asn Ala Pro Ser Gln Leu Ala Val Ala Lys Glu Leu Glu Ser Val
    290                 295                 300

Tyr Leu Asp Ser Asn Arg Tyr Thr Thr Lys Thr Arg Arg Glu Arg Ala
305                 310                 315                 320

Lys Phe Glu Ile Pro Glu Glu Gln Glu Glu Asp Thr Asn Asn Ser Ser
                325                 330                 335

Ser Gly Ser Asn Glu Glu Glu His Glu Ser Leu Asp His Glu Ser Ser
            340                 345                 350

Lys Ser Arg Lys Lys Leu Ser Gly Val Lys Leu Pro Pro Val Arg Asn
        355                 360                 365

Leu Leu Lys Gln Ile Asp Val Phe Asn Gly Pro Lys Arg Val
    370                 375                 380
```

<210> SEQ ID NO 8
<211> LENGTH: 762
<212> TYPE: DNA
<213> ORGANISM: Artificial Sequence
<220> FEATURE:
<223> OTHER INFORMATION: Synthetic sequence

<400> SEQUENCE: 8

```
cttttgttaa tgaggtgaac aaaacaggca acacggcttt acattgggcg tcgttgaatg     60

gcaaattaga cgtggtcaag ctactgtgtg atgaatatga ggcagacccc tttattagaa    120

acaaattcgg ccacgatgct atctttgagg ccgagaacag cgggaaggaa gaagtggaaa    180
```

-continued

```
catacttttt gaagaagtat gatgtcgaac ctgaagatga tgaagaagac acacaaactg    240

agggcaagaa ttcggtccaa atcacaaagg gtacagaaat tgaacaagtc accaaggaag    300

ccaccgaggc tttaagagaa gaaaccgaga aactgaatat aaataaagac taaagtaaag    360

agcttgtttt cttcgtggaa taaaagccgt aatatccatt gagcatgata ttttatttct    420

tggtaccgga gaagataaaa ggatggaacc agcagaaatg cattaataaa tacaaaaaat    480

ttagaaaaga gttacagtaa taatgtatat ttctctcaca aactaagtaa ccgcttcaaa    540

agcgtatatt ttgaatgcat tgaactttcc atttcattac ccgcagagcc ggagtcctca    600

tcaacgacgg agtgaaaaat tttgtaattg cgagaaaaag tgaaattgat ggaaaaaaag    660

aaaaagaaag tagaagaaga cattataaga gagactagga aacttcttgc acatcaaccg    720

aaaagcgcct aggcaaccag tcatataata agcacgcacg ag                       762


<210> SEQ ID NO 9
<211> LENGTH: 352
<212> TYPE: DNA
<213> ORGANISM: Artificial Sequence
<220> FEATURE:
<223> OTHER INFORMATION: Synthetic DNA

<400> SEQUENCE: 9

atttattgga gaaagataac atatcatact ttcccccact tttttcgagg ctcttctata     60

tcatattcat aaattagcat tatgtcattt ctcataacta ctttatcacg ttagaaatta    120

cttattatta ttaaattaat acaaaattta gtaaccaaat aaatataaat aaatatgtat    180

atttgaattt taaaaaaaaa atcctataga gcaaaaggat tttccattat aatattagct    240

gtacacctct tccgcatttt ttgagggtgg ttacaacacc actcattcag aggctgtcgg    300

cacagttgct tctagcatct ggcgtccgta tgtatgggtg tattttaaat aa            352
```